United States Patent
Kyritsis

(10) Patent No.: US 6,902,396 B2
(45) Date of Patent: Jun. 7, 2005

(54) ORTHODONTIC BRACKET AND POSITIONING SYSTEM

(76) Inventor: George Kyritsis, 3086 Dagenias, Laval, Quebec (CA), H7P 1T6

( * ) Notice: Subject to any disclaimer, the term of this patent is extended or adjusted under 35 U.S.C. 154(b) by 15 days.

(21) Appl. No.: 10/434,933

(22) Filed: May 9, 2003

(65) Prior Publication Data
US 2003/0194674 A1 Oct. 16, 2003

Related U.S. Application Data

(63) Continuation-in-part of application No. 09/981,111, filed on Oct. 16, 2001, now Pat. No. 6,592,367.

(51) Int. Cl.[7] .................................................. A61C 7/00
(52) U.S. Cl. ............................................. 433/8; 433/3
(58) Field of Search ........................... 433/8, 9, 10, 11, 433/13, 14, 15, 17, 3

(56) References Cited

U.S. PATENT DOCUMENTS

| | | | |
|---|---|---|---|
| 3,320,525 A | 5/1967 | Forster | 433/9 |
| 3,729,826 A | 5/1973 | Kesling | 32/14 |
| 4,192,070 A | 3/1980 | Lemchen | 433/11 |
| 4,565,526 A | 1/1986 | Kawata et al. | 433/8 |
| 4,585,413 A | 4/1986 | Wool | 433/8 |
| 4,867,678 A | 9/1989 | Parker | 433/8 |
| 4,927,362 A | 5/1990 | Snead | 433/17 |
| 4,948,367 A | 8/1990 | Haas | 433/9 |
| 5,098,288 A | 3/1992 | Kesling | 433/9 |
| 5,169,311 A | 12/1992 | Lee | 433/14 |
| 5,295,823 A * | 3/1994 | Farzin-Nia | 433/9 |
| 5,322,435 A | 6/1994 | Pletcher | 433/11 |
| 5,439,378 A * | 8/1995 | Damon | 433/8 |
| 5,464,349 A | 11/1995 | Andreiko | 433/24 |
| 5,618,175 A | 4/1997 | Reher et al. | 433/8 |
| 5,823,771 A | 10/1998 | Nord | 433/14 |
| 5,971,754 A | 10/1999 | Sondhi | 433/24 |
| 6,086,364 A | 7/2000 | Brunson | 433/10 |
| 6,206,690 B1 | 3/2001 | Vargas | 433/9 |
| 6,368,105 B1 * | 4/2002 | Voudouris et al. | 433/11 |
| 2003/0180678 A1 * | 9/2003 | Kesling et al. | 433/8 |
| 2003/0224310 A1 * | 12/2003 | Andreiko | 433/3 |

* cited by examiner

Primary Examiner—Melba Bumgarner

(57) ABSTRACT

An orthodontic bracket and positioning system for providing a compact and wingless orthodontic bracket. The orthodontic bracket and positioning system includes a base, a bracket member attached to the base, a vertical passage and a horizontal passage within the bracket, and a front slot within the bracket member for receiving an archwire. At least one ligature member extends through the vertical passage and about the archwire for securing the archwire within the front slot. The vertical passage is substantially traverse to the front slot for allowing the ligature member to extend about the archwire substantially traverse to the archwire. A gauge member is utilized to properly orient the orthodontic bracket and positioning system with respect to the longitudinal axis of the tooth.

19 Claims, 11 Drawing Sheets

ORTHODONTIC BRACKET AND POSITIONING SYSTEM

CROSS REFERENCE TO RELATED APPLICATIONS

I hereby claim benefit under Title 35, United States Code, Section 120 of U.S. patent application Ser. No. 09/981,111 filed Oct. 16, 2001. This application is a continuation-in-part of the Ser. No. 09/981,111 application. The Ser. No. 09/981,111 application has been issued by the USPTO as U.S. Pat. No. 6,592,367 The Ser. No. 09/981,111 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to orthodontic bracket devices and more specifically it relates to an orthodontic bracket and positioning system for providing a compact and wingless orthodontic bracket.

2. Description of the Prior Art

Orthodontic braces have been in use for years. Orthodontic braces are utilized for correcting various types of dental problems such as misaligned teeth. Conventional braces are typically comprised of a plurality of brackets secured to the teeth, an archwire that extends between the plurality of brackets, and elastic or metal ligature ties that are secured about the brackets for retaining the archwire within each of the brackets. Additional force generating auxiliary devices may be utilized in conjunction with the brackets and archwire to achieve various types of desirable forces upon the teeth of a patient.

The "archwire" is the main wire that fits into each of the brackets or other attachments, on the outside of an individual's teeth. The archwire also provides most of the forces that move the patient's teeth. The archwire also provides a track along which the teeth move. Elastic ligature are basically small elastic rings that are utilized to attach the archwire to the brackets. Ligatures are comprised of various materials (elastic and non-elastic), sizes and colors.

The brackets are attachments that are bonded to the patient's teeth utilizing various types of adhesives. The brackets transmit the forces from the archwire to the patient's teeth. As shown in FIG. 1 of the drawings, conventional orthodontic brackets are generally comprised of a flat plate member having a plurality of tie wings extending outwardly from thereof defining a horizontal passage for receiving the archwire. There are various designs of orthodontic brackets that utilize the tie wing concept as is well known in the industry. As further shown in FIG. 1 of the drawings, the plurality of tie wings are typically within the four corners of the plate member and may have various shapes and structures for receiving both the archwire and the elastic ligature.

The main problem with conventional orthodontic brackets is that they are relatively large in size and not aesthetically pleasing when positioned upon a patient's teeth. A further problem with conventional orthodontic brackets is that they are prone to collecting debris and food within. Another problem with conventional orthodontic brackets is that they are difficult to bond close the gingival margin of the teeth because of their relative large size and structure.

While these devices may be suitable for the particular purpose to which they address, they are not as suitable for providing a compact and wingless orthodontic bracket. Conventional orthodontic brackets are relatively large and sometimes cause various types of complications for a patient.

In these respects, the orthodontic bracket and positioning system according to the present invention substantially departs from the conventional concepts and designs of the prior art, and in so doing provides an apparatus primarily developed for the purpose of providing a compact and wingless orthodontic bracket.

SUMMARY OF THE INVENTION

In view of the foregoing disadvantages inherent in the known types of orthodontic brackets now present in the prior art, the present invention provides a new orthodontic bracket and positioning system construction wherein the same can be utilized for providing a compact and wingless orthodontic bracket.

The general purpose of the present invention, which will be described subsequently in greater detail, is to provide a new orthodontic bracket and positioning system that has many of the advantages of the orthodontic brackets mentioned heretofore and many novel features that result in a new orthodontic bracket and positioning system which is not anticipated, rendered obvious, suggested, or even implied by any of the prior art orthodontic brackets, either alone or in any combination thereof.

To attain this, the present invention generally comprises a base, a bracket member attached to the base, a vertical passage and a horizontal passage within the bracket, and a front slot within the bracket member for receiving an archwire. At least one ligature member extends through the vertical passage and about the archwire for securing the archwire within the front slot. The vertical passage is substantially traverse to the front slot for allowing the ligature member to extend about the archwire substantially traverse to the archwire. A gauge member is utilized to properly orient the orthodontic bracket and positioning system with respect to the longitudinal axis of the tooth.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an orthodontic bracket and positioning system that will overcome the shortcomings of the prior art devices.

A second object is to provide an orthodontic bracket and positioning system for providing a compact and wingless orthodontic bracket.

A further object is to provide an orthodontic bracket and positioning system for properly aligning the orthodontic bracket with respect to the longitudinal axis of a tooth.

Another object is to provide an orthodontic bracket and positioning system that utilizes beveled or rounded edges thereby providing a smoother contour.

Another object is to provide an orthodontic bracket and positioning system that is aesthetically pleasing for a patient by providing a bracket that is less visible.

An additional object is to provide an orthodontic bracket and positioning system that makes it easier to maintain dental hygiene.

A further object is to provide an orthodontic bracket and positioning system that may be bonded closer to the gingival margin of the teeth than conventional orthodontic brackets.

Another object is to provide an orthodontic bracket and positioning system that does not utilize tie wings.

A further object is to provide an orthodontic bracket and positioning system that may be constructed significantly smaller than conventional orthodontic brackets utilizing tie wings.

Another object is to provide an orthodontic bracket and positioning system that reduces the problems associated with conventional brackets such as gingival inflammation, lip ulceration, collection of debris and food, and tooth decalcification.

A further object is to provide an orthodontic bracket and positioning system that increases the overall comfort and confidence within the patient.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
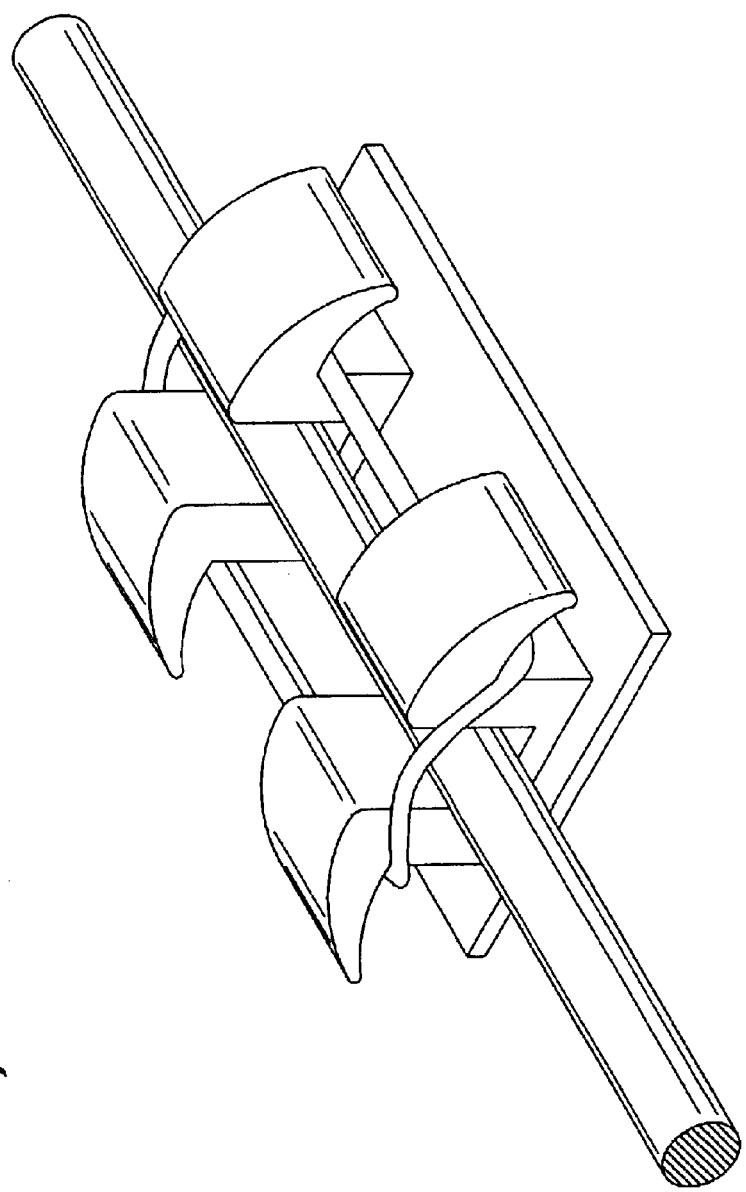
FIG. 1 is an upper perspective view of the prior art orthodontic bracket with an archwire positioned between the tie wings and an elastic ligature securing the archwire within the bracket.

Turning now descriptively to the drawings, in which similar reference characters denote similar elements throughout the several views, FIGS. 2 through 8 illustrate an orthodontic bracket and positioning system 10, which comprises a base 20, a bracket member 30 attached to the base 20, a vertical passage 32 and a horizontal passage 31 within the bracket, and a front slot 34 within the bracket member 30 for receiving an archwire 40. At least one ligature member 50 extends through the vertical passage 32 and about the archwire 40 for securing the archwire 40 within the front slot 34. The vertical passage 32 is substantially traversed with respect to the front slot 34 for allowing the ligature member 50 to extend about the archwire 40 substantially traverse to the archwire 40. A gauge member 60 is utilized to properly orient the orthodontic bracket and positioning system 10 with respect to the longitudinal axis of the tooth 12.

As shown in FIGS. 2 through 8 of the drawings, the base 20 is comprised of a flat structure having a front surface 22 and a rear surface 24. The rear surface 24 of the base 20 is secured to the outer surface of the tooth 12 utilizing a conventional adhesive or bonding technique. The base 20 may have various shapes and sizes other than illustrated within FIGS. 2 through 8 of the drawings. The base 20 is preferably comprised of a mesh structure, however a solid material may also be utilized to construct the base 20. The base 20 may be comprised of various types of materials, colors and structures as can be appreciated.

As best shown in FIGS. 2, 3, 5 and 6 of the drawings, the bracket member 30 is secured to the front surface 22 of the base 20 opposite of the tooth 12. The bracket member 30 may be secured to the base 20 utilizing various securing methods. Additionally, the bracket member 30 and the base 20 may be constructed from a single solid structure thereby requiring no additional attachment thereof. The bracket member 30 may be comprised of various types of materials, colors and transparencies. The bracket member 30 may also have various other shapes and designs other than that illustrated within FIGS. 1 through 8 of the drawings.

As shown in FIGS. 2, 3, 5 and 8 of the drawings, a vertical passage 32 extends through a rear portion of the bracket member 30 for receiving at least one ligature member 50. The vertical passage 32 preferably has a rectangular cross sectional shape, however various other shapes may be utilized such as but not limited to circular, square, oval, and triangular. The vertical passage 32 may have various widths, however the vertical passage 32 is preferably sufficient in size to receive at least one ligature member 50. The vertical passage 32 preferably extends in a vertical manner through the rear portion of the bracket member 30 substantially traverse to the front slot 34.

A horizontal passage 31 extends through a rear portion of the bracket member 30 substantially transverse with respect to the vertical passage 32 for receiving at least one ligature member 50. The horizontal passage 31 preferably has a rectangular cross sectional shape, however various other shapes may be utilized such as but not limited to circular, square, oval, and triangular. The horizontal passage 31 may have various widths, however the horizontal passage 31 is preferably sufficient in size to receive at least one archwire 40 or ligature member 50. The horizontal passage 31 preferably extends in a horizontal manner through the rear portion of the bracket member 30 substantially parallel to the front slot 34.

Figure 3:
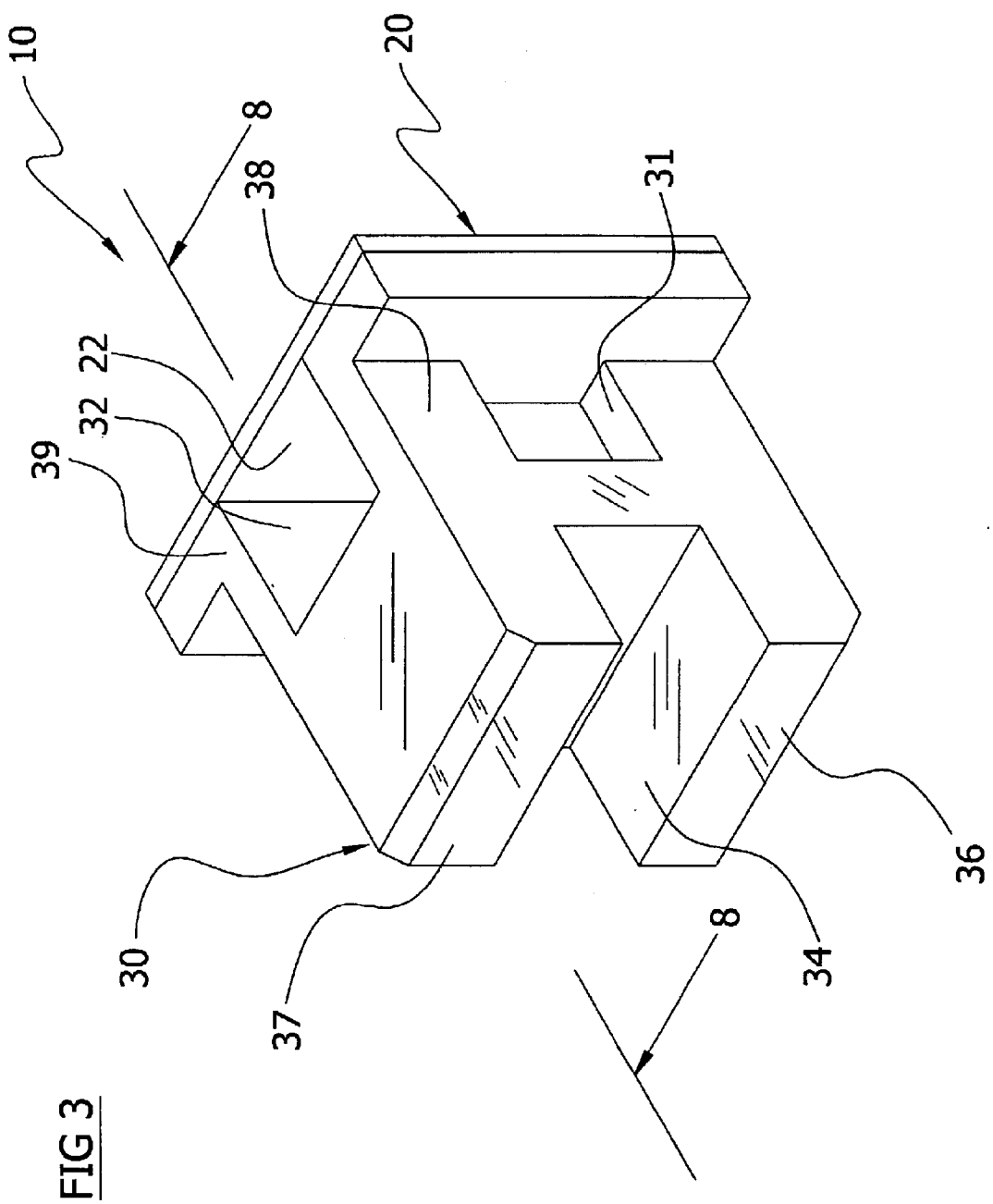
FIG. 3 is an upper perspective view of the present invention with beveled front edges.

As best shown in FIG. 3 of the drawings, the bracket member 30 includes a first wall 38 and a second wall 39 extending from the base 20 in opposition to one another thereby defining the sides of the vertical passage 32. The walls 38, 39 are preferably substantially parallel to one another as best shown in FIG. 3 of the drawings.

Figure 4:
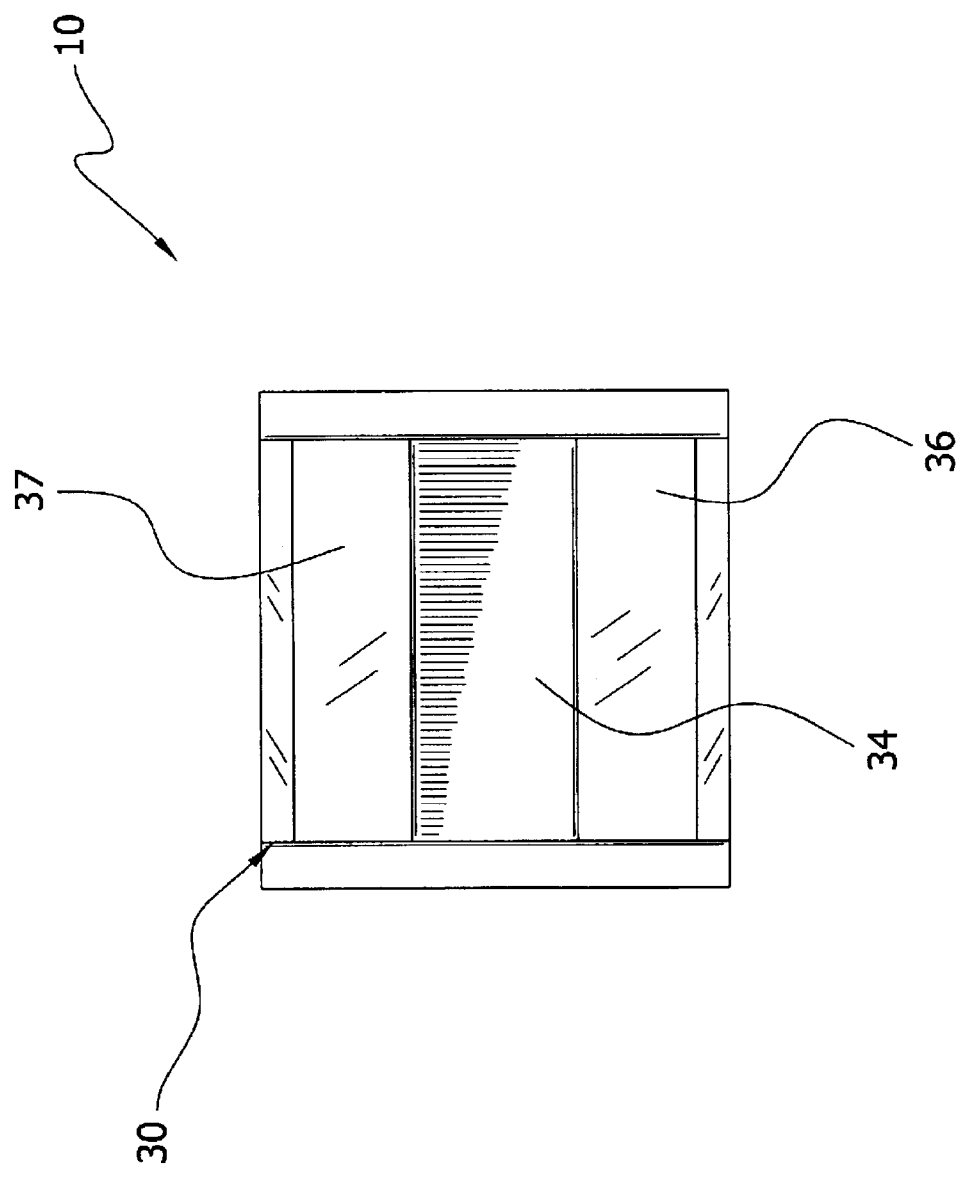
FIG. 4 is a front view of the present invention.
Figure 5:
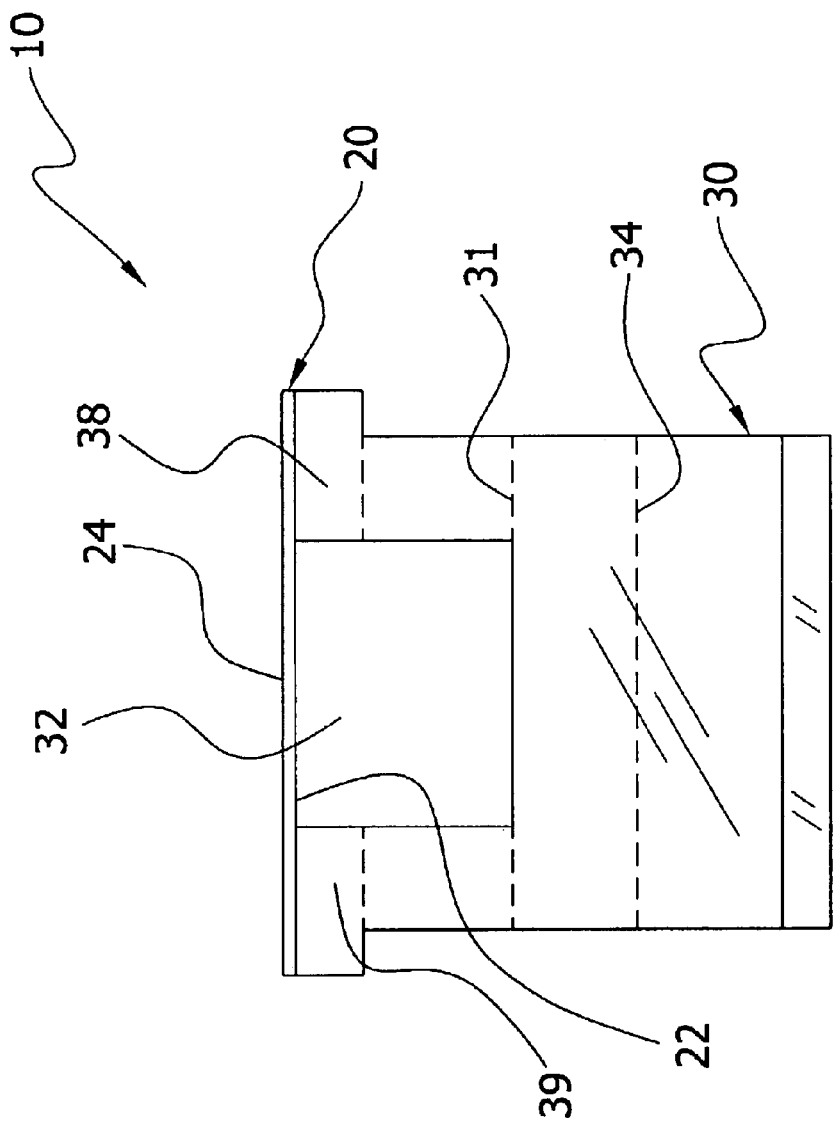
FIG. 5 is a top view of the present invention illustrating the vertical passageway for receiving the ligature wires.
Figure 8:
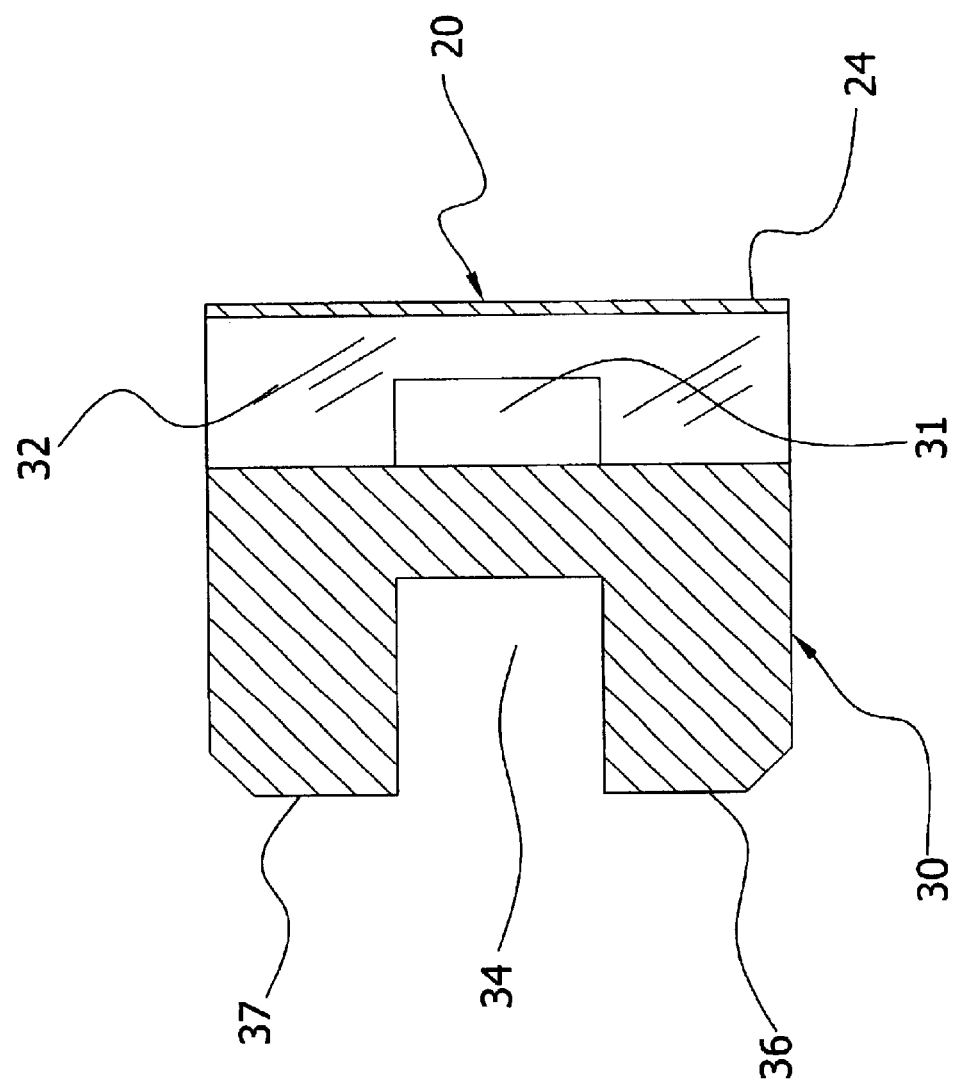
FIG. 8 is a cross sectional view taken along line 8—8 of FIG. 3.

The walls 38, 39 are enclosed by a traverse wall portion as shown in FIGS. 3 and 8 of the drawings. As shown in FIGS. 3 through 5 of the drawings, the portion of the walls 38, 39 engaging the base 20 are preferably flanged outwardly thereby providing an increased surface area for securing the bracket member 30 to the base 20 without obstructing the vertical passage 32.

Figure 6:
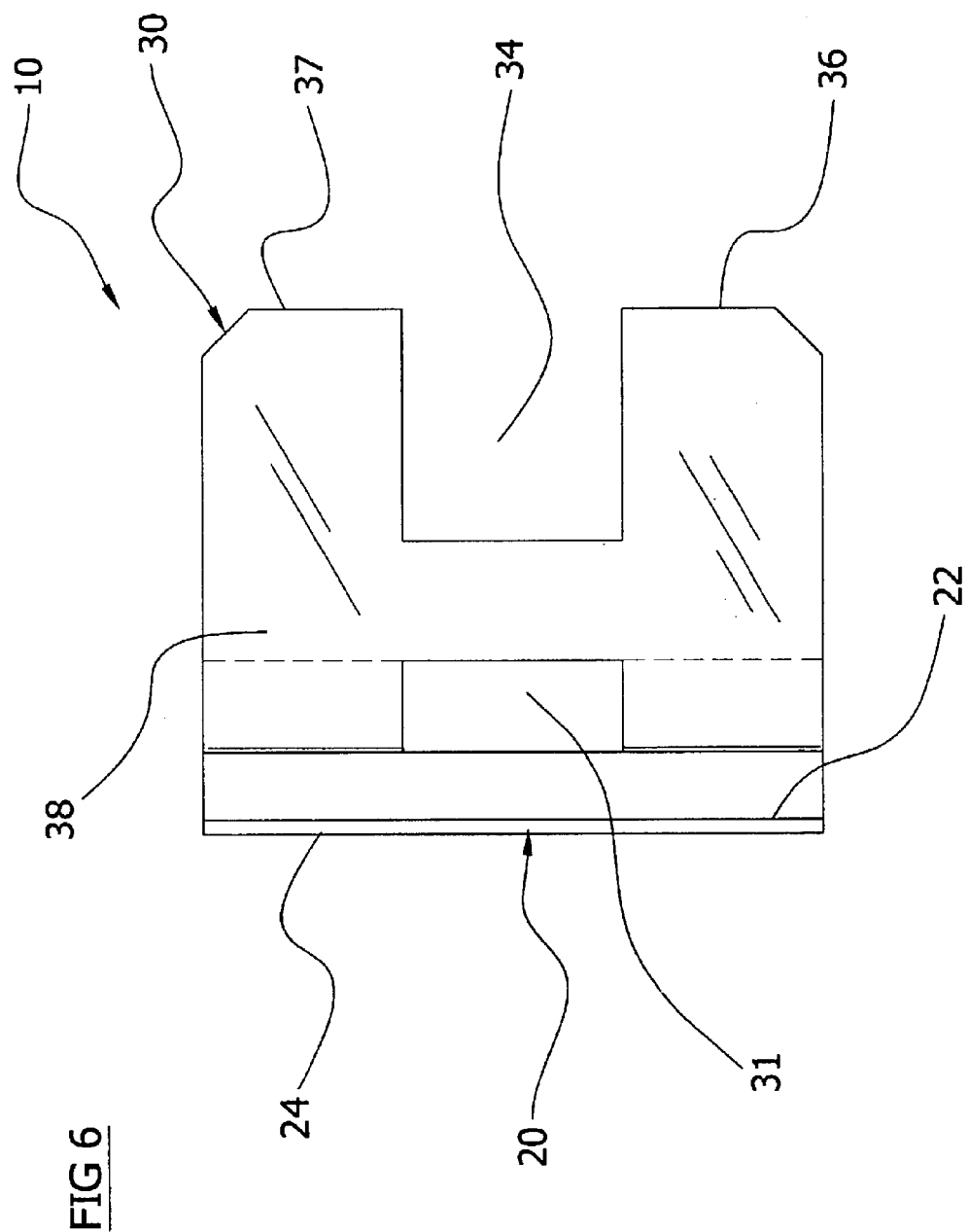
FIG. 6 is a side view of the present invention illustrating the horizontal slot for receiving the archwire.
Figure 7:
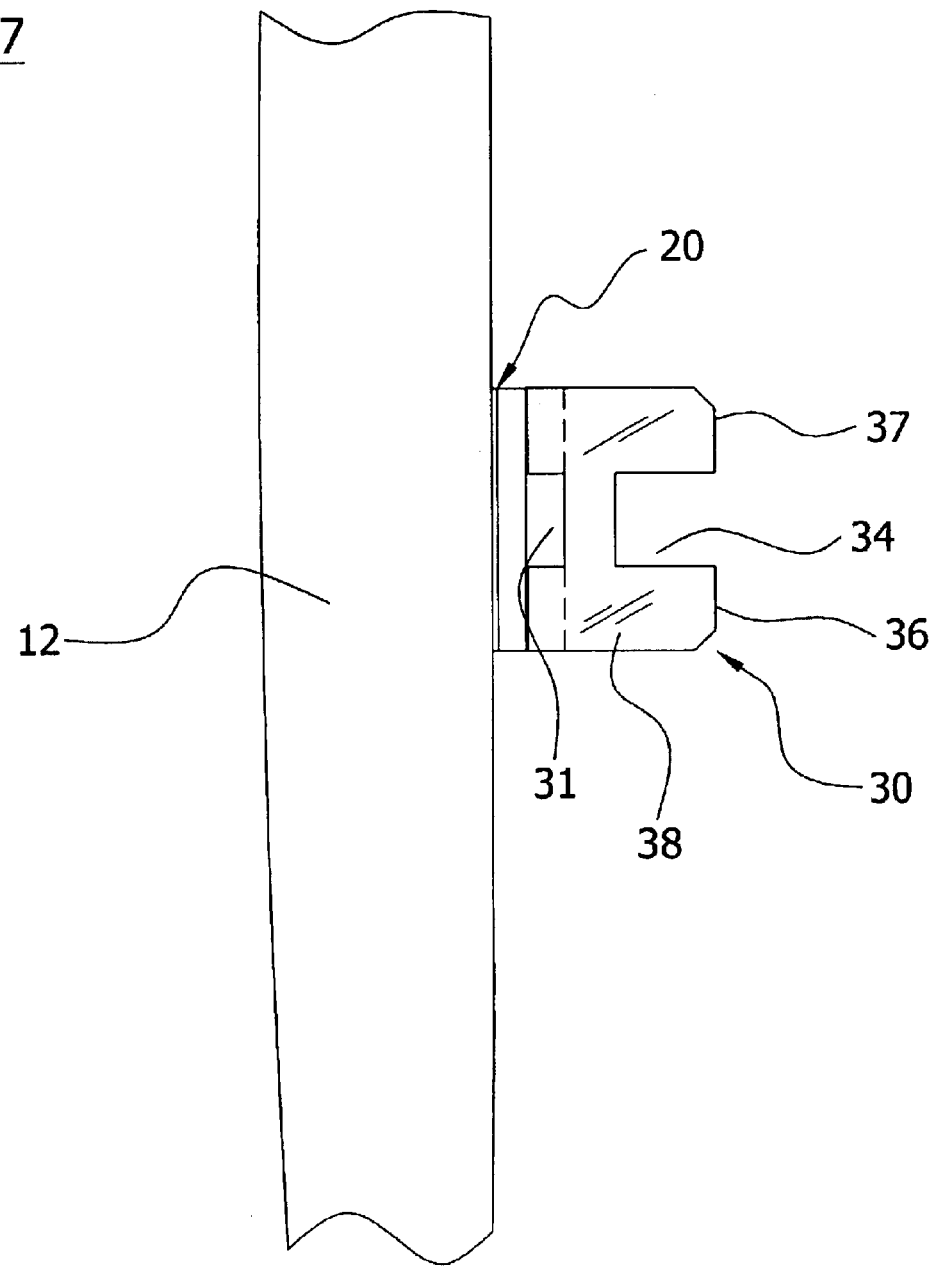
FIG. 7 is a side view of the present invention attached to a tooth.
Figure 11:
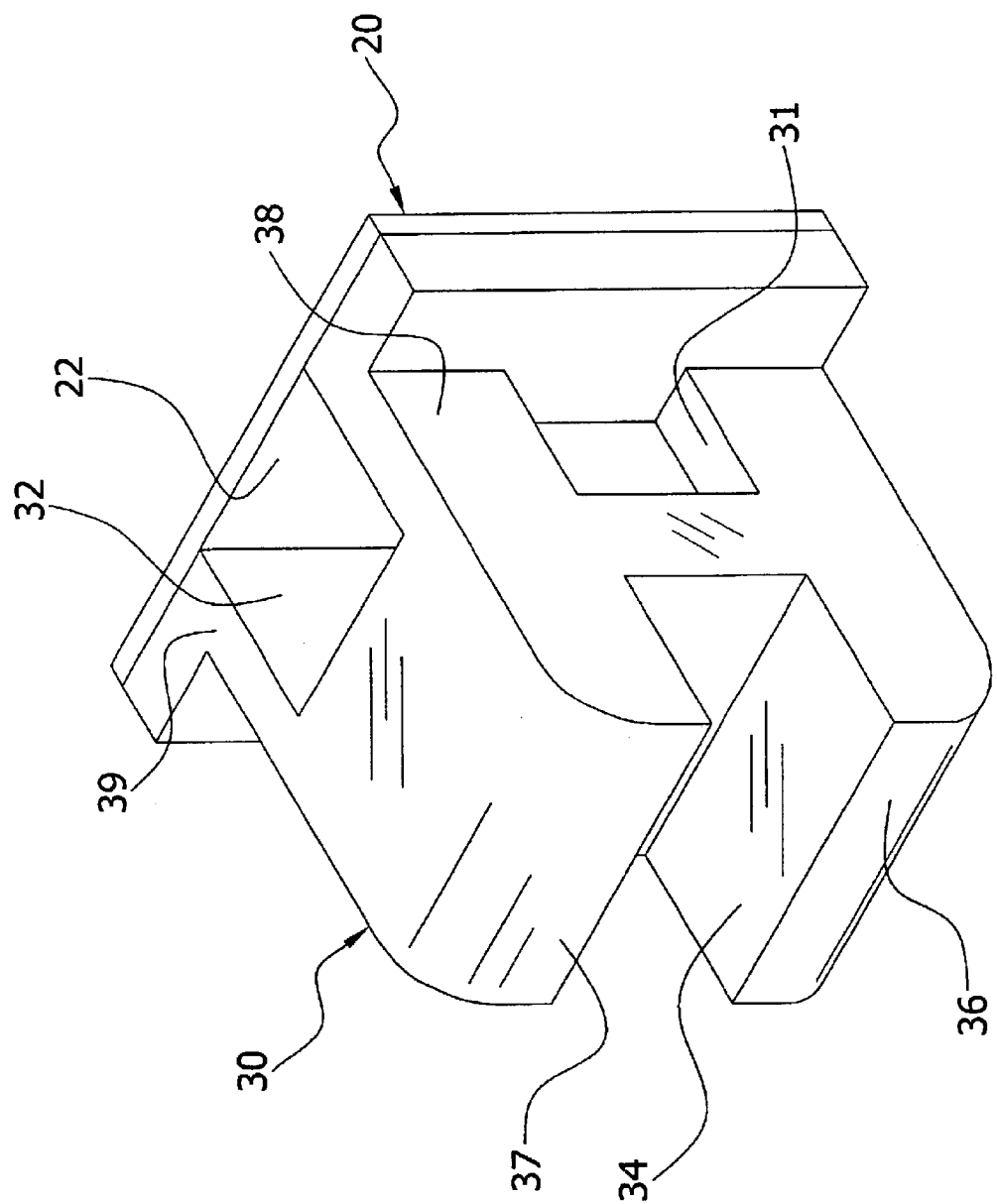
FIG. 11 is an upper perspective view of the present invention with rounded front edges.

As further shown in FIG. 3 of the drawings, a lower extension 36 and an upper extension 37 extend forwardly from the traverse wall portion. The extensions 36, 37 are preferably parallel to one another as best illustrated in FIGS. 3 and 6 of the drawings. The extensions 36, 37 preferably are each comprised of a relatively broad width and a relatively narrow height thereto. The extensions 36, 37 preferably have a flat front portion for preventing the collection of debris and food. The extensions 36, 37 preferably have beveled edges as illustrated in FIG. 3 or rounded edges as illustrated in FIG. 11.

Figure 2:
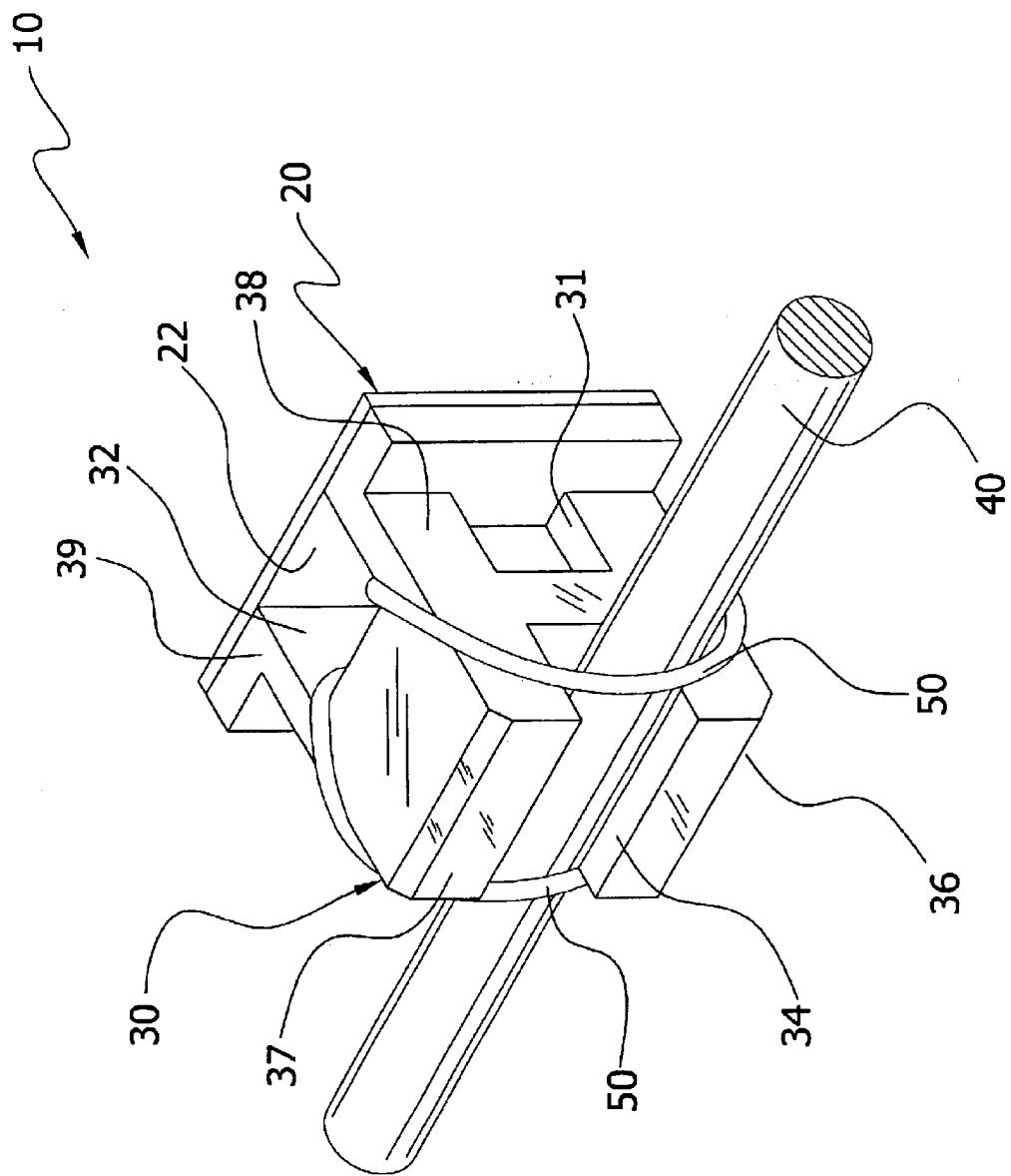
FIG. 2 is an upper perspective view of the present invention containing an archwire within.

As further shown in FIGS. 3, 4, 6, 7 and 8 of the drawings, the opposing extensions 36, 37 define a front slot 34 between thereof for receiving a portion of the archwire 40. As shown in FIG. 6 of the drawings, the front slot 34 has a rectangular cross section, however various other cross sectional shapes may be utilized to construct the front slot 34. In addition, the front slot 34 is preferably sufficient in depth and height to receive the archwire 40 as best illustrated in FIG. 2 of the drawings. The front slot 34 is preferably substantially traverse with respect to the vertical passage 32 as shown in FIG. 3 of the drawings.

As shown in FIG. 2 of the drawings, a pair of ligature members 50 are secured within the bracket member 30 and the archwire 40. The ligature members 50 may be comprised of various types of materials such as but not limited to coated or non-coated metal wire. Each ligature member 50 has an elongate structure with opposing ends which are tied together after positioning within the vertical passage 32 and about the archwire 40.

Figure 9:
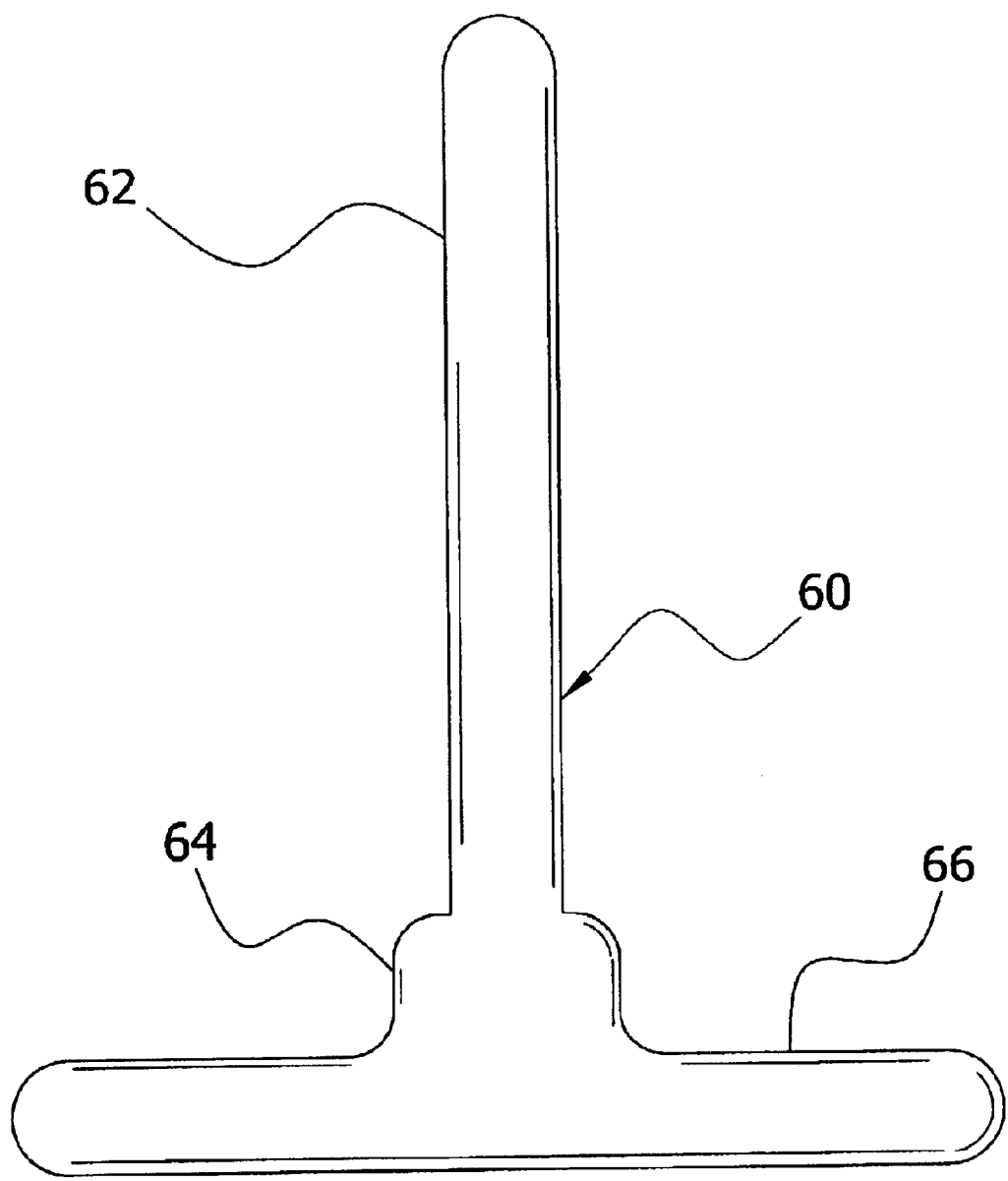
FIG. 9 is a front view of the gauge member.
Figure 10:
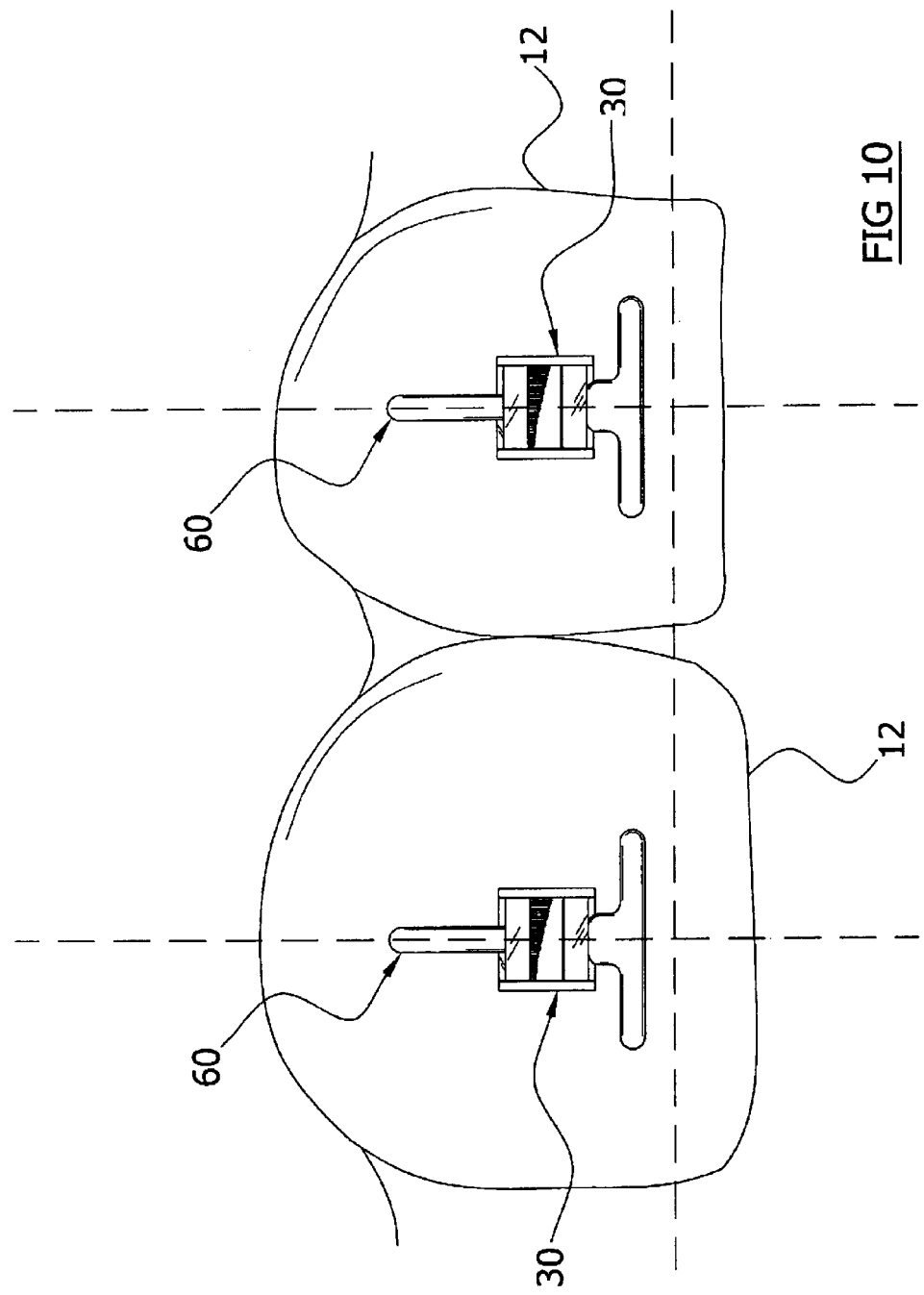
FIG. 10 is a front view of the gauge members being utilized to position the brackets along a longitudinal axis of the teeth.

FIG. 9 illustrates a gauge member 60 which assists in the alignment of the orthodontic bracket system 10 upon the surface of the tooth 12. The gauge member 60 preferably has a T-shaped structure with a shaft portion 62 and a handle portion 66. A flanged portion 64 preferably extends outwardly from the shaft portion near the intersection of the handle portion 66 and the shaft portion 62. The flanged portion 64 prevents the gauge member 60 from being inserted too far into the vertical passage 32. The shaft portion 62 is inserted into the vertical passage 32 of the bracket member 30 and utilized to manipulate and visually indicate the alignment with the longitudinal axis of the tooth as best illustrated in FIG. 10 of the drawings. After the bracket member 30 has been properly secured to the tooth 12, the gauge member 60 is thereafter removed from the bracket member 30.

In use, the dental professional secures the bracket member 30 to a tooth 12 by applying an adhesive between the rear surface 24 of the base 20 and the tooth 12. The gauge member 60 is utilized to ensure that the bracket member 30 is properly positioned. The adhesive is allowed to cure and the dental professional continues securing additional bracket members 30 to the teeth 12 of the patient as required. The dental professional then positions the archwire 40 within the front slots 34 of each of the bracket members 30 as shown in FIG. 2 of the drawings. One or more ligature members 50 are then extended through the vertical passage 32 and bent about the side portions of the extensions 36, 37 as further shown in FIG. 2 of the drawings. The ligature members 50 are then tightened to the desired tautness and then are secured by twisting or tying the opposing distal ends of each ligature member 50. The archwire 40 is thereby retained within the front slot 34 by the ligature members 50 and allowed to slide longitudinally within the front slot 34 if required.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An orthodontic bracket system, comprising:
   a bracket member having a rear portion and a front portion, wherein said rear portion is attachable to a tooth;
   a vertical passage extending vertically through said rear portion of said bracket member, wherein said vertical passage is defined by a first wall, a second wall, a base extending between said first wall and said second wall, and a traverse wall portion extending between said first wall and said second wall opposite of said base;
   a horizontal passage extending horizontally through said rear portion of said bracket member; and
   a front slot extending into said front portion of said bracket member, wherein said front slot is positioned substantially horizontally within said front portion for receiving a portion of an archwire;
   wherein said bracket member includes a lower extension and an upper extension defining said front slot;
   wherein said first wall and said second wall each have a flanged portion attached to said base;
   a gauge member having a T-shaped structure removably positionable within said vertical passage for aligning said bracket member with respect to a longitudinal axis of a tooth, wherein said gauge member is comprised of an elongated shaft portion, a handle portion orthogonally attached to an end of said elongated shaft portion, and a flanged portion extending outwardly from said elongated shaft portion near an intersection of said handle portion and said shaft portion.

2. The orthodontic bracket system of claim 1, wherein said vertical passage has a rectangular cross sectional shape.

3. The orthodontic bracket system of claim 1, wherein said horizontal passage is substantially transverse with respect to said vertical passage.

4. The orthodontic bracket system of claim 1, wherein said lower extension and said upper extension have beveled outer edges.

5. The orthodontic bracket system of claim 1, wherein said lower extension and said upper extension have rounded outer edges.

6. The orthodontic bracket system of claim 1, wherein said base is comprised of a mesh material.

7. The orthodontic bracket system of claim 1, wherein said lower extension and said upper extension are substantially parallel to one another.

8. The orthodontic bracket system of claim 1, wherein said front slot has a rectangular cross sectional shape.

9. The orthodontic bracket system of claim 1, wherein horizontal passage is comprised of a rectangular structure.

10. An orthodontic bracket and positioning system, comprising:
   a bracket member having a rear portion and a front portion, wherein said rear portion is attachable to a tooth;
   a vertical passage extending vertically through said rear portion of said bracket member;
   a front slot extending into said front portion of said bracket member, wherein said front slot is positioned substantially horizontally within said front portion for receiving a portion of an archwire; and
   a gauge member having a T-shaped structure removably positionable within said vertical passage for aligning said bracket member with respect to a longitudinal axis of a tooth, wherein said gauge member is comprised of an elongated shaft portion, a handle portion orthogonally attached to an end of said elongated shaft portion, and a flanged portion extending outwardly from said elongated shaft portion near an intersection of said handle portion and said shaft portion.

11. The orthodontic bracket and positioning system of claim 10, wherein said vertical passage is defined by a first wall, a second wall, a base extending between said first wall and said second wall, and a traverse wall portion extending between said first wall and said second wall opposite of said base.

12. The orthodontic bracket and positioning system of claim 10, wherein said vertical passage has a rectangular cross sectional shape.

13. The orthodontic bracket and positioning system of claim 10, a horizontal passage extending horizontally through said rear portion of said bracket member, wherein said horizontal passage is substantially transverse with respect to said vertical passage.

14. The orthodontic bracket and positioning system of claim 10, wherein said bracket member includes a lower extension and an upper extension defining said front slot and wherein said lower extension and said upper extension have beveled outer edges.

15. The orthodontic bracket and positioning system of claim 10, wherein said bracket member includes a lower extension and an upper extension defining said front slot and wherein said lower extension and said upper extension have rounded outer edges.

16. The orthodontic bracket and positioning system of claim 10, wherein said vertical passage is defined by a first wall, a second wall, a base extending between said first wall and said second wall, and a traverse wall portion extending between said first wall and said second wall opposite of said base, wherein said base is comprised of a mesh material.

17. The orthodontic bracket and positioning system of claim 10, wherein said bracket member includes a lower extension and an upper extension defining said front slot and wherein said lower extension and said upper extension are substantially parallel to one another.

18. The orthodontic bracket and positioning system of claim 10, wherein said front slot has a rectangular cross sectional shape.

19. An orthodontic bracket system, comprising:
   a bracket member having a rear portion and a front portion, wherein said rear portion is attachable to a tooth;
   a vertical passage extending vertically through said rear portion of said bracket member;
   a horizontal passage extending horizontally through said rear portion of said bracket member;
   a front slot extending into said front portion of said bracket member, wherein said front slot is positioned substantially horizontally within said front portion for receiving a portion of an archwire; and
   at least one ligature member securable within said vertical passage and about said archwire, wherein said ligature member is comprised of an elongate structure having opposing ends and is comprised of a flexible material;
   wherein said bracket member includes a lower extension and an upper extension defining said front slot, wherein said lower extension and said upper extension each have a rectangular structure with a longitudinal axis parallel to said front slot;
   wherein said vertical passage is defined by a first wall, a second wall, a base extending between said first wall and said second wall, and a traverse wall portion extending between said first wall and said second wall opposite of said base; wherein said first wall and said second wall each have a flanged portion attached to said base;
   wherein said vertical passage has a rectangular cross sectional shape;
   wherein said base is comprised of a mesh material;
   wherein said lower extension and said upper extension are substantially parallel to one another; and
   wherein said front slot has a rectangular cross sectional shape;
   a gauge member having a T-shaped structure removably positionable within said vertical passage for aligning said bracket member with respect to a longitudinal axis of a tooth, wherein said gauge member is comprised of an elongated shaft portion, a handle portion orthogonally attached to an end of said elongated shaft portion, and a flanged portion extending outwardly from said elongated shaft portion near an intersection of said handle portion and said shaft portion.

* * * * *